United States Patent [19]

Yao

[11] Patent Number: 5,562,097
[45] Date of Patent: Oct. 8, 1996

[54] USER CONTROL FOR STEERABLE CW DOPPLER

[75] Inventor: Lin X. Yao, Bellevue, Wash.

[73] Assignee: Siemens Medical Systems, Inc., Iselin, N.J.

[21] Appl. No.: 282,948

[22] Filed: Oct. 11, 1994

[51] Int. Cl.$^6$ .................................................. A61B 8/06
[52] U.S. Cl. ............................................ 128/662.01
[58] Field of Search ............ 128/660.07, 661.08–661.1, 128/662.01, 661.01

[56] References Cited

U.S. PATENT DOCUMENTS

| | | | |
|---|---|---|---|
| 4,416,286 | 11/1983 | Iinuma et al. | 128/663 |
| 4,438,652 | 3/1984 | Saito | 73/861.25 |
| 4,460,924 | 7/1984 | Lippel | 358/310 |
| 4,543,599 | 9/1985 | Willis et al. | 358/13 |
| 4,598,589 | 7/1986 | Riley et al. | 73/609 |
| 4,622,978 | 11/1986 | Matsuo et al. | 128/662.01 X |
| 4,651,745 | 3/1987 | Namekawa et al. | 128/663 |
| 4,758,893 | 7/1988 | Lippel | 358/209 |
| 4,764,748 | 8/1988 | Geen et al. | 340/347 |
| 4,812,846 | 3/1989 | Noro | 341/131 |
| 4,915,115 | 4/1990 | Sasaki et al. | 128/660.05 |
| 5,016,641 | 5/1991 | Schwartz | 128/661.09 |
| 5,398,216 | 3/1995 | Hall et al. | 128/661.08 X |
| 5,454,372 | 10/1995 | Banjanin et al. | 128/661.08 |

*Primary Examiner*—Francis Jaworski

[57] ABSTRACT

A method and apparatus of operating an ultrasound imaging apparatus so as to obtain continuous wave (CW) Doppler data from a user selected area comprises operating a multiple element transducer array and its associated delay and signal processing circuitry so as to develop and display in substantially real-time a two-dimensional ultrasound image, operating a user controllable device so as to cause a display of at least one controllable position marker in substantially real-time within the displayed two-dimensional ultrasound image, which marker selects an area of sensitivity within the ultrasound image for which it is desired to obtain CW Doppler data, operating the multiple element transducer array and its associated delay signal processing circuitry based upon the position of the selected area so that, 1) a given number of the multiple elements are used to transmit a steered beam of CW ultrasound through the selected area, and
2) a given number of the multiple elements of the array are used to receive a steered receive beam which also passes through the selected area.

21 Claims, 2 Drawing Sheets

USER CONTROL FOR STEERABLE CW DOPPLER

BACKGROUND OF THE INVENTION

1. Field of the Invention

This invention relates to ultrasonic Doppler diagnostic devices having a continuous wave (CW) Doppler mode, and in particular, to a method and apparatus for user selection of a Doppler sensitive portion of an imaged area and subsequent control of the CW Doppler mode for obtaining Doppler information from the user selected area.

2. Description of the Prior Art

The ultrasonic Doppler method is widely used for non-invasively detecting and measuring movement within a body, and finds wide use in medical ultrasound scanners for non-invasive diagnostic analysis of blood flow within a patient, e.g., for the detection and measurement of blood flow within the heart, blood vessels, etc., of a patient.

There are basically two operational modes of ultrasound Doppler; continuous wave (CW) and pulsed (PW). The PW mode is particularly useful for obtaining velocity data used to form a two-dimensional blood flow image (color flow image). However, because the pulse repetition rate (PRF) of PW Doppler systems limits the maximum flow velocity which can be determined without aliasing, the CW mode is found to be particularly useful for obtaining velocity data to accurately determine relatively high flow velocities.

Additionally, diagnostic ultrasound devices conventionally develop a so-called B-mode image, which is basically a two dimensional tomographic image, as well known to those skilled in the art. The B-mode image is formed using a transducer which can scan an area, and conventionally uses, as also well known in the art, one of several types of multiple element transducer arrays, such as a linear array of 64 or 128 transducer elements. On the other hand, CW Doppler operation generally requires the use of a special transducer probe which has two transducers, one for transmission and one for reception (as also well known in the art and commonly referred to as a pencil probe). It is desirable, for the sake of simplicity, to use a single probe and its receive signal processing circuitry to obtain the data useful for not only the Doppler mode, but also the B-mode. One technique to accomplish this is described in U.S. Pat. No. 4,915,115 entitled "Ultrasonic Imaging Apparatus for Displaying B-Mode and Doppler-Mode Images" and issued Apr. 10, 1990 to Sasaki et al. As described therein, data is obtained by first operating the transducer array via conventional transmit/receive control circuitry so as to provide steering and focusing of the transmitted ultrasound pulses and for providing appropriate individual delays to the received signals so that a conventional beamformer and image processor can create the B-mode image. Thereafter, the user can observe the B-mode image, and mark the image using a cursor with an indication of the beam direction and depth along that beam direction from which PW Doppler data is desired to be obtained. Then, the transducer is operated in the PW Doppler mode so as to receive Doppler signals therefrom, using range-gating techniques, and in turn develop Doppler data. It is noted that the CW Doppler mode is not described by Sasaki et al. Instead, Sasaki et al. is concerned with the reception efficiency of the transducer when it is desirable to operate it in both of the Doppler and B-mode, and solves this problem by providing an ultrasonic transducer having two peaks in its reception efficiency characteristic curves, one centered at the frequency used for B-mode imaging and the other centered at the frequency used for PW Doppler data gathering.

Using a multi-element transducer array for the CW Doppler mode is desirable because the ability to control transmit beam steering and focusing, as well as reception beam steering and focusing results in improved signal-to-noise (S/N) performance, as well as an opportunity to better select the Doppler sample volume (the overlap regions between the CW transmit and receive beams). U.S. Pat. No. 4,598,589 entitled "Method of CW Doppler Imaging Using Variably Focused Ultrasonic Transducer Array" and issued Jul. 8, 1986 to Riley et al. describes circuitry for operating such a multi-element transducer array so as to obtain improved S/N CW Doppler images, however, there is no indication about how a user of the apparatus would select or control the CW Doppler beam steering and/or focusing. The conventional techniques used for PW Doppler such as found in the forenoted U.S. Pat. No. 4,915,115 or in U.S. Pat. No. 4,416,286 entitled "Ultrasound Blood Flow Measuring Apparatus" issued Nov. 22, 1983 to Iinuma et al., would not be usable since CW Doppler does not use a range gate and therefore a selection of "depth" along a given receive beam line is inappropriate.

It is an object of the present invention to facilitate the use of a CW Doppler mode of operation for an ultrasound imaging apparatus which uses a multi-element transducer array.

It is a further object of the invention to provide a user control for selecting a CW Doppler sensitive area within a displayed two-dimensional ultrasound image.

It is a still further object of the invention to provide such a user control in a simple and low cost arrangement as well as in a way which can be easily controlled by the user.

These and other objects of the invention will become apparent from the following detailed description of a preferred embodiment of the invention, the accompanying drawings and the claims.

SUMMARY OF THE INVENTION

A method and apparatus of operating an ultrasound imaging apparatus so as to obtain continuous wave (CW) Doppler data from a user selected area comprises operating a multiple element transducer array and its associated delay and signal processing circuitry so as to develop and display in substantially real-time a two-dimensional ultrasound image, operating a user controllable device so as to cause a display of at least one controllable position marker in substantially real-time within said displayed two-dimensional ultrasound image, which marker selects an area of sensitivity within said ultrasound image for which it is desired to obtain CW Doppler data, operating the multiple element transducer array and its associated delay and signal processing circuitry based upon the position of the selected area so that, 1) a given number of said multiple elements of said array are used to transmit a steered beam of CW ultrasound through said selected area, and
2) a given number of said multiple elements of said array are used to receive a steered receive beam which also passes through said selected area; and processing the receive beam so that a Doppler display is generated from the receive beam, which is representative of movement within said selected area.

In accordance with a further aspect of the invention, the given number of multiple elements of the array that are used to transmit and receive respective steered beams of CW ultrasound through said selected area, are also used to focus the steered transmit and receive beams at said selected area.

DETAILED DESCRIPTION OF THE INVENTION

Figure 1:
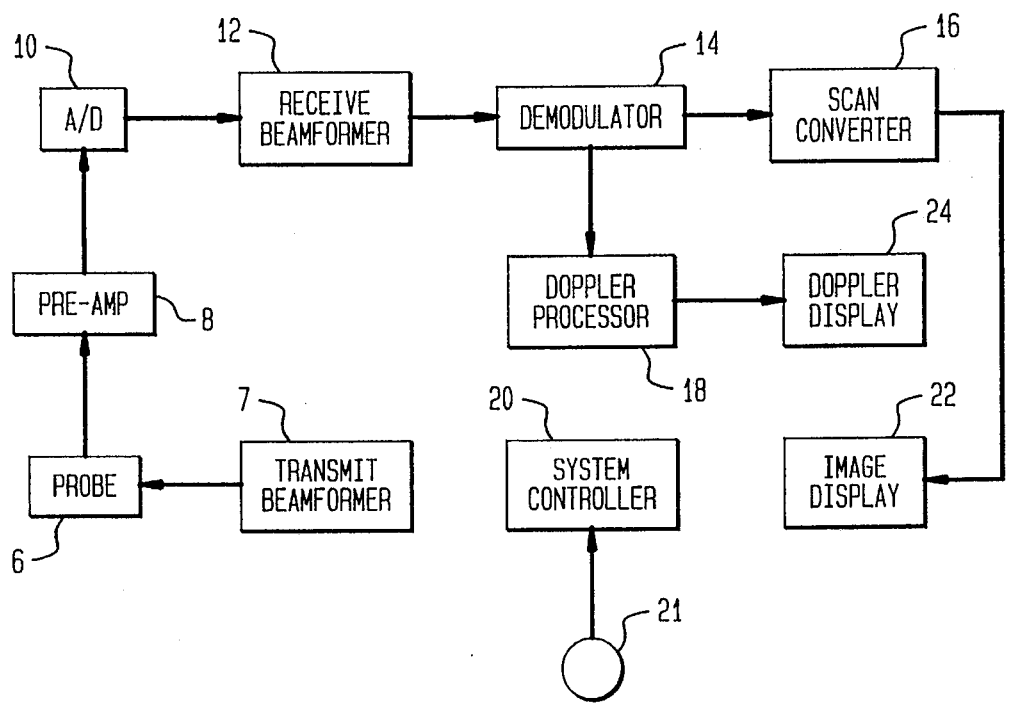
FIG. 1 is a block diagram of a medical ultrasound system in which the present invention may be used.

FIG. 1 illustrates in block diagram from a medical ultrasound imaging system in which the present invention may be used. The system comprises an ultrasound probe 6 including a multi-element ultrasonic transducer having multiple piezoelectric transducer elements arranged in, for example, a linear array, a transmit beamformer 7, an analog pre-amplifier section 8 and an A/D conversion stage 10. Additionally, the system comprises a digital receive beamformer 12, a demodulator 14, a scan converter 16, a Doppler processor 18 and a system controller 20. As well known, transmit beamformer 7 includes controllable delay means for causing controllable focusing and steering of ultrasound beams which are transmitted into the patient via the probe 6, and receive beamformer 12 includes controllable delay means for forming, via controllable focusing and steering, receive beams from received echoes resulting from reflections of the ultrasound beams transmitted into the patient, all under the control of system controller 20.

System controller 20 includes user interface means 21 including devices such as a keyboard, trackball, switches, etc. (not specifically shown), through which an operator of the system may place the system in a B-imaging (the so-called Brightness) mode, a PW Doppler mode, a simultaneous B- imaging/PW Doppler mode or a CW Doppler mode. In the B-imaging mode, beamformer 12 produces RF signals at its output that represent the strength of the ultrasound echoes received along a series of scanning lines spread through a cross-section of the patient's body. These RF signals are demodulated by demodulator 14, the demodulator essentially performing a detection function on the RF signals produced during the B-imaging mode. The resulting detected image signal provided at the output of demodulator 14 is passed to scan converter 16. As well known, the scan converter accumulates echo data for a plurality of scan lines that make up a single frame of the image. For a sector scan format, the scan converter also converts such data into a rectangular raster scan format suitable for display on a video monitor. Successive image frames are then displayed in real time on a video image display 22.

When the system is set by the user to a PW Doppler mode, the operator marks the position of a sample volume from which the PW Doppler data is to be collected, by examining and marking the B-mode image. The marked volume is correlated to a sample cell at a selected range along a selected scan line, while for CW Doppler, the Doppler sensitive volume is conventionally cylindrical and extends along the length of the scan line. However, in the disclosed preferred embodiment which uses a multi-element transducer array, focused and steered CW Doppler beams are possible, and therefor with appropriate control of the transmit and receive delays it is possible to have a CW Doppler sensitive volume which comprises an overlap of the focussed and steered CW transmit and CW receive beams. Receive beamformer 12 then generates a continuous RF beam line representative of the echo signals received from the beam direction which includes the selected Doppler sensitive volume. Demodulator 14 converts the RF beam line signals produced during the Doppler mode to baseband or to an intermediate frequency, and produces demodulated in-phase (I) and quadrature (Q) signals at its output which are provided to Doppler processor 18. These I and Q signals are collectively referred to as the "Doppler signal". Doppler processor 18 processes the Doppler signal and provides signals to a Doppler display 24 which may include a video display for displaying a video output of the spatial characteristics of the Doppler signal (i.e., a Doppler image) on a video display, as well as an audio output that is converted to an audible sound by a Doppler audio display, such as speakers (not specifically shown). The construction and operation of a substantial portion of each of the individual components described above are well known by those of ordinary skill in the art, and therefore further description of their construction and operation, other than as needed to understand the present invention, is omitted. For example, the forenoted U.S. Pat. No. 4,598,589, incorporated herein by reference, discloses such prior art control for developing CW Doppler images using, however, analog signal processing techniques.

Figure 2:
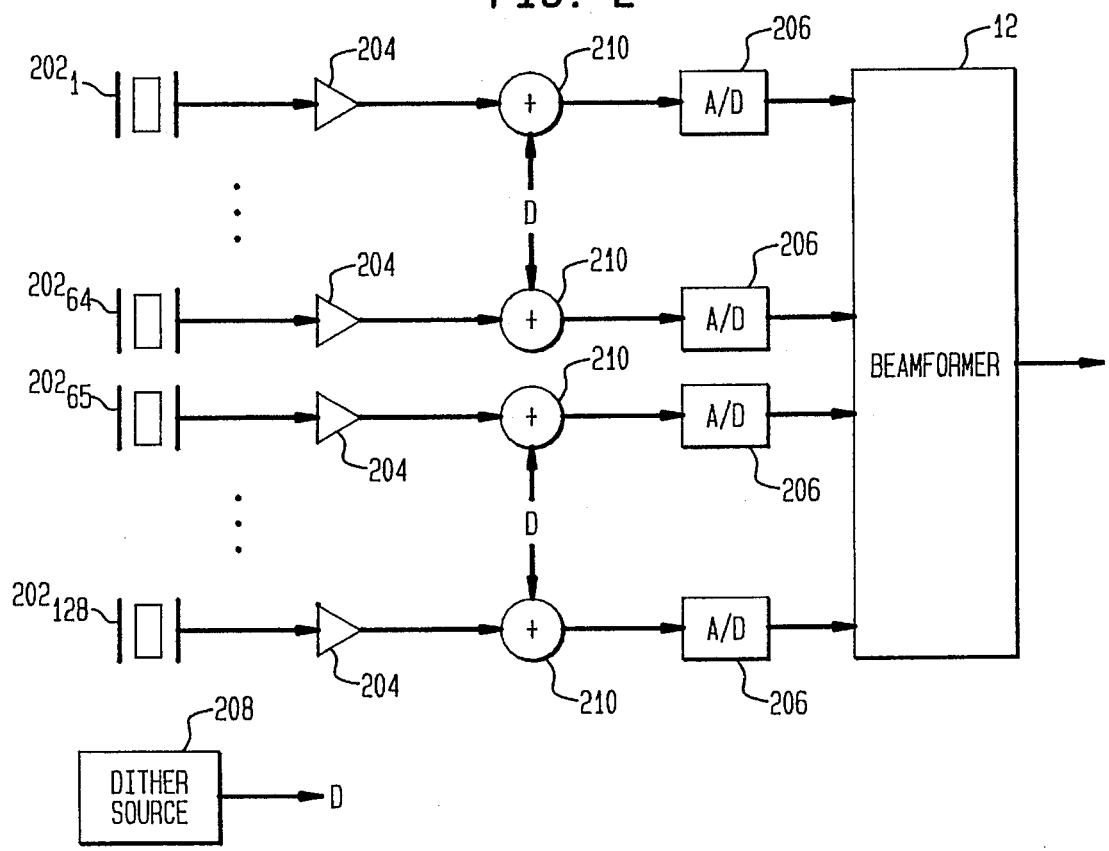
FIG. 2 is a block diagram of a portion of the front end of the medical ultrasound system shown in FIG. 1.

FIG. 2 illustrates details of construction for portions of the ultrasound apparatus of FIG. 1 using a digital beamformer. A digital beamformer is particularly useful for the present invention in that it allows relatively straightforward microprocessor control of beam steering and focusing. Where appropriate, the same reference numbers are used to indicate the same portions of the ultrasound apparatus. For clarity purposes, only the receive portions of the medical ultrasound apparatus are shown, the transmit portions being omitted in that they are of conventional digital design and operation. As shown in FIG. 2, the probe includes a plurality of individual transducer elements 202. Each element 202 is connected to a signal processing channel comprising an analog pre-amplifier 204 and an A/D converter 206 which provides a digitized received ultrasound echo signal to the digital beamformer 12. As noted previously with respect to FIG. 1, receive beamformer 12 provides an appropriate delay to each of the received and digitized ultrasound echo signals so that they can be coherently combined to form an ultrasound beam line 22.

A dither signal source 208 provides a common dither signal D which is added to each received echo beam signal before digitization by A/D converters 206, via an adder 210 which is included in each channel just before the A/D converter 206. Dithering of the A/D converters increases their ability to detect a lower amplitude signal, thereby effectively increasing the dynamic range of the A/D converters. This increase, although particularly useful when operating the apparatus in the CW Doppler mode, may also find use while operating the apparatus in the PW Doppler mode.

As well known by those familiar with A/D converters, the dither signal causes extra transitions of the least significant bit (LSB) of the digital signal developed by A/D converters 206. The dither signal source 208 provides a dither signal having an amplitude which causes the LSB to vary +/−0.5

LSB. As a result of an averaging operation, preferably located at a point near the output of the signal processing apparatus (described in conjunction with the box car filters of FIG. 4), there is an apparent increase in resolution of the A/D conversion.

In a preferred embodiment, the dither signal is caused to be sinusoidal, so it can be easily removed by filters which already exist in Doppler processor 18, such as wall filters, to be described later on. This way, the dither signal itself does not degrade the S/N performance of the A/D converters, while a random noise dither signal would degrade the S/N performance.

Figure 3:
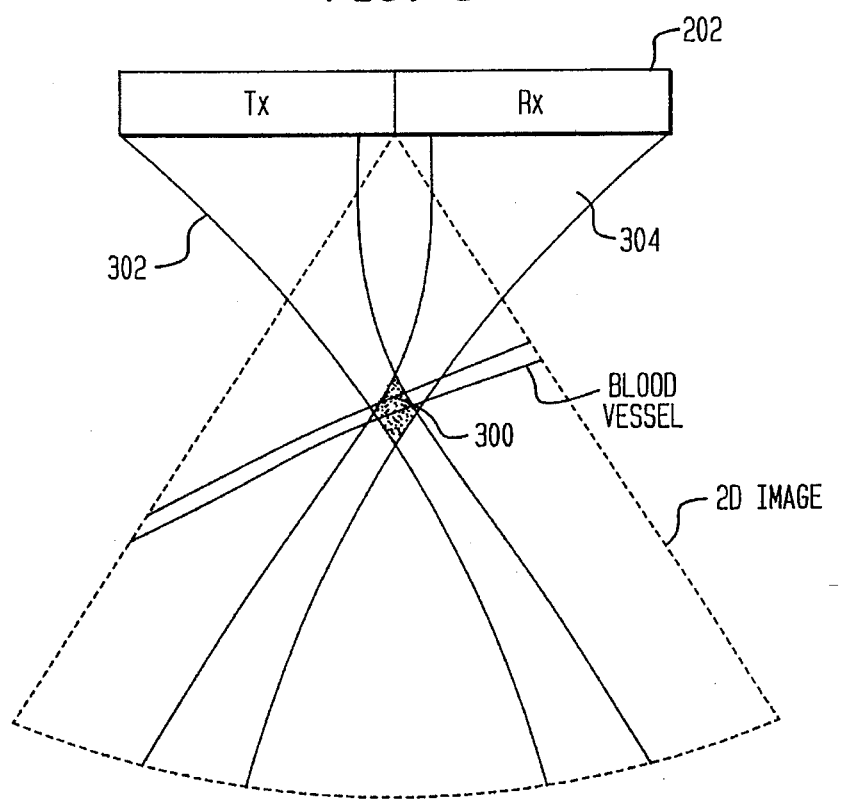
FIG. 3 is an illustration of how a CW Doppler sensitive area is selected in accordance with the principles of the invention using the apparatus of FIG. 1.

In the preferred embodiment probe 6 includes 128 transducer elements 202 wherein 64 adjacent elements, and their respective transmit and receive signal processing channels, are used for transmitting a focussed and steered CW ultrasound beam (for example at 4 mHz) into the body of a patient and the next 64 channels are used for controllably receiving a focussed CW Doppler beam which is steered so as to intersect the transmitted beam a given depth within the patients body, such as shown in FIG. 3.

In accordance with principles of the invention, a user of the apparatus can operate a controllable interface device 21, such as a track ball, while viewing a displayed real-time two-dimensional ultrasound image, for selecting a CW Doppler sensitive area 300 of the displayed image from which it is desired to obtain Doppler data. Once the area is selected, the system controller 20 provides appropriate delays to the transmit and receive beamformers 7 and 12 so as to control the steering and preferably also the focussing of the transmit 302 and receive 304 beams in order that they overlap at the selected area and thereby obtain Doppler data representative of movement in that volume of the body. The obtaining of the CW Doppler data is preferably carried out in a time division multiplexed manner with B-mode and/or color flow imaging.

Since both the transmit and receive beams are focused so as to overlap the same volume in the body, the receive beamformer will be much more sensitive to this area than other volumes in the body. This overlap volume is therefore called as a Doppler sensitive volume (or Doppler sensitive area when being referred to as a selected portion of a two-dimensional display of an ultrasound image). This technique not only greatly improves the position uncertainty problem normally found in conventional CW Doppler imaging, but is easy to implement and is simple for an operator to control.

During operation, the ultrasound apparatus is caused to develop a conventional B-mode image of a blood vessel and/or other anatomy. The user will then operate a controllable device 21, such as a trackball, to move an "x" or other marker to a region of interest in the vessel. The two arms of the "x" represent the direction of the transmit and receive beam, respectively, at the selected region. Therefore, the angle between the two arms of the "x" will change in accordance with the location of the "x" relative to the transmit and receiving aperatures of the probe. The present invention allows the user can adjust the position of the probe and/or the "x" marker in order to optimize the CW Doppler angle while at the same time watching the vessel anatomy and the transmit and receive beam directions.

Additionally, in accordance with a further aspect of the invention, the user can also adjust the focusing of one or both of the transmit and receiving beams, in order to better ocntrol the size of the selected Doppler sensitive area. With each change of focus there would be a corresponding change in the size of the displayed "x", (the wider the focusing, the larger the Doppler sensitive area and the larger the displayed "x"). With this technique the S/N performance at a user selectable volume within the body can be maximized.

Thus, in accordance with the present invention, the system controller 20 operates the ultrasound apparatus for causing the steering angle and focus for both of the transmit and receive beams to be controlled according to the user selection of the Doppler sensitive area.

Figure 4:
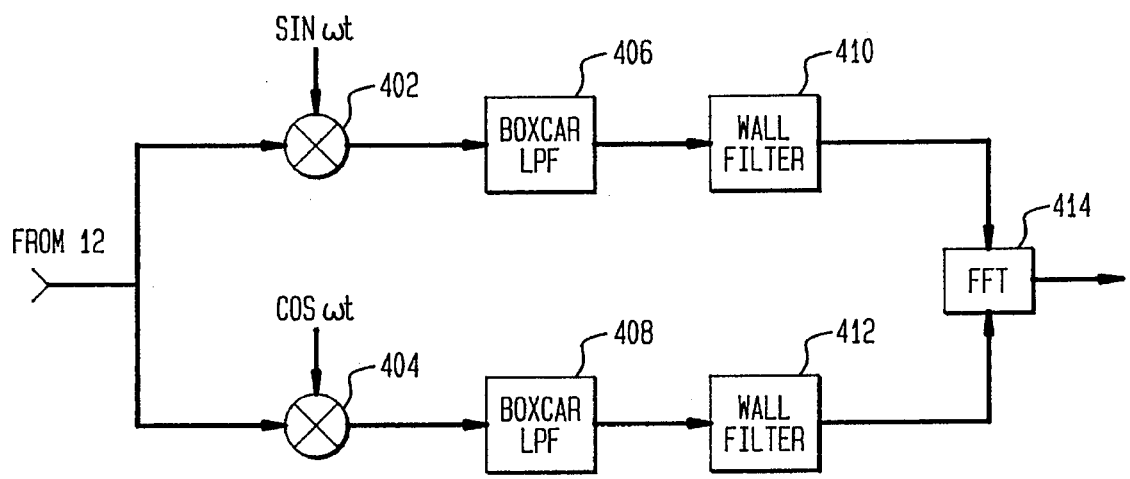
FIG. 4 is a block diagram of the demodulator and Doppler processor portions of the ultrasound system shown in FIG. 1.

FIG. 4 illustrates the demodulator and Doppler processor portions of the ultrasound system shown in FIG. 1, configured by system controller 20 for processing the CW Doppler signals and developing Doppler data for display therefrom. More specifically, the demodulator portion 14 includes mixers 402 and 404 which are driven by quadrature sinusoidal signals having the frequency of the transmitted CW Doppler ultrasound signal (e.g. 4 mHz) for developing quadrature I and Q demodulated Doppler signals. Low pass filtering of the I and Q signals is conventionally required in order to remove the $2f_0$ frequency components, and in the present embodiment the low pass filters are constructed as box car filters 406 and 408 which accumulate and decimate the digital signals provided by mixers 402 and 404, respectively. As well known by those of ordinary skill in digital signal processing technology, box car filtering is essentially the accumulation or summation of a plurality of digital signal samples and then an averaging of the samples by dividing the accumulation sum by the number of samples accumulated, and finally decimation so as to provide a single multi-bit (i.e., 24 bit) digital word at its output. In the present embodiment, 504 digital signal samples are used to generate each digital word output from the box car filters. Each digital word is representative of one of, for example, 128 points along a selected beam line.

The I and Q outputs are then applied to Doppler processor 18, which as well known to those of ordinary skill in the art, comprises wall filter processing of the I and Q signals using wall filters 410 and 412 and, as one way of obtaining spectrum information, applying the output of the wall filters to a fast fourier transform (FFT) processor 414. FFT processor 414 provides at its output a signal representing the frequency spectrum of the Doppler signal which can be applied to audio speakers for "displaying" the Doppler data, or to one-half of a video screen, so as to display a Doppler image along side the B-mode image. As well known, wall filters 410, 412 can comprise high pass filters which cut-off the unwanted lower frequencies, including the forenoted sinusoidal dither signal. The Doppler signal at the output of FFT processor 414 is then provided to the Doppler display which includes a video monitor and audio speakers for presenting the Doppler information to the system operator.

The length of box car filters 406, 408 are set so that the box car length (accumulation interval) comprises an integer number times the number of samples of the clutter signal/cycle. That is, if for example, the A/D converter sample rate is 36 mHz and the CW Doppler signal frequency is 4 mHz, there will be 9 A/D samples/cycle of the Doppler signal. Therefore, the number of samples averaged by the box car filters for determining each Doppler data point, i.e., the box car length, should be an integer number times 9, such as 504 which is 56×9. This is important in that the clutter signal causes a periodicity to occur in the quantization error of the A/D converter, which, due to the relatively high amplitude of the clutter signal, may easily have an amplitude which is an order of magnitude greater than the amplitude of the Doppler signal that the apparatus is trying to detect. By making the length of the box car filter an integer multiple of the number of A/D samples/cycle of the ultrasound frequency, the error over the box car length becomes a constant, and therefore no longer hinders detection of the low level Doppler signal.

Thus, there has been shown and described a novel method and apparatus for providing controllably obtaining CW Doppler information in an ultrasound imaging apparatus which satisfies all the objects and advantages sought therefor. Many changes, modifications, variations and other uses and applications of the subject invention will, however, become apparent to those skilled in the art after considering this specification and its accompanying drawings which disclose preferred embodiments thereof. For example, although in the illustrated embodiment a B-mode image is described as being viewed by the user to select the Doppler sensitive area, a color flow image could also be used, or an overlap of both the B-mode and the color flow images. Additionally, other shapes and sizes could be used as equivalent to an "x" marker, such as a parallelogram box having controllably sized dimensions. All such changes, modifications, variations and other uses and applications which do not depart from the spirit and scope of the invention are deemed to be covered by the invention which is limited only by the claims which follow.

I claim:

1. A method for operating an ultrasound imaging apparatus for obtaining continuous wave (CW) Doppler data from a user selected area, comprising:
   operating a multiple element transducer array and associated controllable delay and signal processing circuitry so as to develop and display in substantially real-time a two-dimensional ultrasound image;
   operating a user controllable device so as to cause a display of at least one controllable area marker in substantially real-time within said displayed two-dimensional ultrasound image, which area marker is of a position and size controllable by the operator, the marker position and size indicative of an area of sensitivity within said ultrasound image for which it is desired to obtain CW Doppler data;
   operating said multiple element transducer array and its associated delay and signal processing circuitry based upon the user selected position of said area of sensitivity so that,
   1) a given number of said multiple elements are used to transmit a steered beam of CW ultrasound through said selected area of sensitivity,
   2) a given number of said multiple elements of said array are used to receive a steered receive beam which also passes through said user selected area of sensitivity; and
      processing said receive beam so that a Doppler image display is generated from the receive beam, which is representative of movement within said user selected area of sensitivity.

2. The method of claim 1, wherein said first-mentioned operating step develops and displays a B-mode image.

3. The method of claim 1, wherein said first-mentioned operating step develops and displays a color flow image.

4. The method of claim 2, wherein said first-mentioned operating step develops and displays a color flow image which overlaps said B-mode image.

5. The method of claim 1, wherein said third-mentioned operating step operates the multiple elements and their associated delay and signal processing circuitry so that the transmitted steered beam is also focused based on the position of said user selected area of sensitivity.

6. The method of claim 5, wherein said third-mentioned operating step operates the multiple elements and their associated delay and signal processing circuitry so that the received steered beam is also focused based on the position of said user selected area of sensitivity.

7. The method of claim 1, wherein said third-mentioned operating step operates the multiple elements and their associated delay and signal processing circuitry so that the received steered beam is focused based on the position of said user selected area of sensitivity.

8. The method of claim 1, further comprising the step of displaying shape and direction of each of the transmit beam and the receive beam, and wherein the area marker is an area of intersection of the transmit and receive beam.

9. The method of claim 1, in which the area marker position and size generally coincides with the area of increased sensitivity.

10. The method of claim 1, in which the area marker comprises the area of increased sensitivity.

11. The method of claim 1, in which the area of increased sensitivity comprises the area marker.

12. A method for operating an ultrasound imaging apparatus for obtaining continuous wave (CW) Doppler data from a user selected area, comprising:
   operating a multiple element transducer array and associated controllable delay and signal processing circuitry so as to develop and display in substantially real-time a two-dimensional ultrasound image;
   operating a user controllable device so as to cause a display of at least one controllable position marker in substantially real-time within said displayed two-dimensional ultrasound image, which marker selects an area of sensitivity within said ultrasound image for which it is desired to obtain CW Doppler data;
   operating said multiple element transducer array and its associated delay and signal processing circuitry based upon the user selected position of said area of sensitivity so that,
   1) a given number of said multiple elements are used to transmit a steered beam of CW ultrasound through said selected area of sensitivity,
   2) a given number of said multiple elements of said array are used to receive a steered receive beam which also passes through said user selected area of sensitivity; and
      processing said receive beam so that a Doppler image display is generated from the receive beam, which is representative of movement within said user selected area of sensitivity; and
      wherein said user controllable device operates so that the controllable position marker which is displayed comprises at least an "X", wherein each arm of the "X" is representative of a respective one of the transmit and receive beam directions based on the position of said user selected area.

13. A method for operating an ultrasound imaging apparatus for obtaining continuous wave (CW) Doppler data from a user selected area, comprising:
   operating a multiple element transducer array and associated controllable delay and signal processing circuitry so as to develop and display in substantially real-time a two-dimensional ultrasound image;
   operating a user controllable device so as to cause a display of at least one controllable position marker in substantially real-time within said displayed two-dimensional ultrasound image, which marker selects an area of sensitivity within said ultrasound image for which it is desired to obtain CW Doppler data;

operating said multiple element transducer array and its associated delay and signal processing circuitry based upon the user selected position of said area of sensitivity so that, 1) a given number of said multiple elements are used to transmit a steered beam of CW ultrasound through said selected area of sensitivity, 2) a given number of said multiple elements of said array are used to receive a steered receive beam which also passes through said user selected area of sensitivity; and processing said receive beam so that a Doppler image display is generated from the receive beam, which is representative of movement within said user selected area of sensitivity; and wherein said user controllable device operates so that the controllable position marker which is displayed comprises a parallelogram box shaped equivalent to an "X", wherein the box is representative of the size of the user selected area as determined by the focusing and steering of the transmit and receive beams.

14. An ultrasound imaging apparatus for obtaining continuous wave (CW) Doppler data from a user selected area of a body under examination, comprising:

a multiple element transducer array;

delay circuitry coupled to said array for controlling the steering of transmit and receive beams of ultrasound energy into and from, respectively, said body;

signal processing circuitry coupled to the delay circuitry and responsive to the receive beams for developing an image signal;

a display coupled to the signal processing circuitry and responsive to the image signal for displaying in substantially real-time a two-dimensional ultrasound image of a portion of said body;

a user controllable device coupled to said display for controllably positioning at least one controllable area marker which is displayed substantially real-time within said displayed two-dimensional ultrasound image, which marker is positioned and sized by the user to select an area of sensitivity within said ultrasound image for which it is desired to obtain CW Doppler data; and control means coupled to said delay circuitry and responsive to the user selection of the position of the Doppler sensitive area via said user controllable device for causing, 1) a given number of said multiple elements to transmit a steered beam of CW ultrasound through said user selected area of sensitivity, and 2) a given number of said multiple elements of said array to receive a steered receive beam of ultrasound energy which also passes through said user selected area of sensitivity, processing said receive beam so that a Doppler image display is generated from the receive beam, which is representative of movement within said user selected area of sensitivity.

15. An ultrasound imaging apparatus according to claim 14, wherein said delay circuitry is coupled to said array for also controlling the focusing of at least one of the transmit and receive beams.

16. An ultrasound imaging apparatus according to claim 14, wherein said signal processing circuitry processes said receive beam so as to develop a Doppler image signal which causes a Doppler image to be displayed on said display which is representative of movement within said user selected area of sensitivity.

17. The apparatus of claim 14, in which shape and direction of each of the transmit beam and the receive beam are displayed, and wherein the area marker is an area of intersection of the transmit and receive beam.

18. The apparatus of claim 14, in which the area marker position and size generally coincides with the area of increased sensitivity.

19. An ultrasound imaging apparatus for obtaining continuous wave (CW) Doppler data from a user selected area of a body under examination, comprising:

a multiple element transducer array;

delay circuitry coupled to said array for controlling the steering of transmit and receive beams of ultrasound energy into and from, respectively, said body;

signal processing circuitry coupled to the delay circuitry and responsive to the receive beams for developing an image signal;

a display coupled to the signal processing circuitry and responsive to the image signal for displaying in substantially real-time a two-dimensional ultrasound image of a portion of said body;

a user controllable device coupled to said display for controllably positioning at least one controllable position marker which is displayed substantially real-time within said displayed two-dimensional ultrasound image, which marker is positioned by the user to select an area of sensitivity within said ultrasound image for which it is desired to obtain CW Doppler data; and control means coupled to said delay circuitry and responsive to the user selection of the position of the Doppler sensitive area via said user controllable device for causing, 1) a given number of said multiple elements to transmit a steered beam of CW ultrasound through said user selected area of sensitivity, and 2) a given number of said multiple elements of said array to receive a steered receive beam of ultrasound energy which also passes through said user selected area of sensitivity; and wherein said user controllable device causes said controllable position marker to be displayed as at least an "X", wherein each arm of the "X" is representative of a respective one of the transmit and receive beam directions based on the position of said user selected area, as controlled by said user controllable device.

20. An ultrasound imaging apparatus for obtaining continuous wave (CW) Doppler data from a user selected area of a body under examination, comprising:

a multiple element transducer array;

delay circuitry coupled to said array for controlling the steering of transmit and receive beams of ultrasound energy into and from, respectively, said body;

signal processing circuitry coupled to the delay circuitry and responsive to the receive beams for developing an image signal;

a display coupled to the signal processing circuitry and responsive to the image signal for displaying in substantially real-time a two-dimensional ultrasound image of a portion of said body;

a user controllable device coupled to said display for controllably positioning at least one controllable position marker which is displayed substantially real-time within said displayed two-dimensional ultrasound image, which marker is positioned by the user to select an area of sensitivity within said ultrasound image for which it is desired to obtain CW Doppler data; and control means Coupled to said delay circuitry and responsive to the user selection of the position of the Doppler sensitive area via said user controllable device for causing,
1) a given number of said multiple elements to transmit a steered beam of CW ultrasound through said user selected area of sensitivity, and
2) a given number of said multiple elements of said array to receive a steered receive beam of ultrasound energy which also passes through said user selected area of sensitivity;
wherein said user controllable device operates causes said controllable position marker to be displayed as a parallelogram box shaped equivalent to an "X", wherein the box is representative of the size of the user selected area as determined by the focusing and steering of the transmit and receive beams.

21. An ultrasound imaging apparatus for obtaining continuous wave (CW) Doppler data from a user selected area of a body under examination, comprising:

a multiple element transducer array;

delay circuitry coupled to said array for controlling the steering of transmit and receive beams of ultrasound energy into and from, respectively, said body;

signal processing circuitry coupled to the delay circuitry and responsive to the receive beams for developing an image signal;

a display coupled to the signal processing circuitry and responsive to the image signal for displaying in substantially real-time a two-dimensional ultrasound image of a portion of said body;

a user controllable device coupled to said display for controllably positioning at least one controllable position marker which is displayed substantially real-time within said displayed two-dimensional ultrasound image, which marker is positioned by the user to select an area of sensitivity within said ultrasound image for which it is desired to obtain CW Doppler data; and control means coupled to said delay circuitry and responsive to the user selection of the position of the Doppler sensitive area via said user controllable device for causing,
1) a given number of said multiple elements to transmit a steered beam of CW ultrasound through said user selected area of sensitivity, and
2) a given number of said multiple elements of said array to receive a steered receive beam of ultrasound energy which also passes through said user selected area of sensitivity, and
wherein said user controllable device is coupled to said display to cause the size of said displayed controllable position marker to be varied in accordance with the size of the user selected area as determined by the steering and/or focusing of the transmit and receive beams.

* * * * *